US005664599A

United States Patent [19]

Hunt

[11] Patent Number: 5,664,599
[45] Date of Patent: Sep. 9, 1997

[54] FLOW CONTROLLER FOR A PARTICLE SENSOR

[75] Inventor: D. John Hunt, Grants Pass, Oreg.

[73] Assignee: Met One, Inc., Grants Pass, Oreg.

[21] Appl. No.: 664,123

[22] Filed: Jun. 14, 1996

[51] Int. Cl.⁶ ............................................. F16K 24/00
[52] U.S. Cl. ............................ 137/171; 137/593; 210/188
[58] Field of Search ................................. 137/171, 593; 210/188; 604/122

[56] References Cited

U.S. PATENT DOCUMENTS

| | | |
|---|---|---|
| 4,102,655 | 7/1978 | Jeffery et al. |
| 4,585,465 | 4/1986 | Suzuki et al. |
| 4,643,746 | 2/1987 | Suzuki et al. |
| 5,123,938 | 6/1992 | Nobel |
| 5,332,100 | 7/1994 | Jameson ............................... 209/164 |
| 5,338,341 | 8/1994 | Mazzei et al. ......................... 96/208 |
| 5,379,791 | 1/1995 | Christopher ........................... 137/1 |
| 5,422,003 | 6/1995 | Kataoka ................................ 210/188 |
| 5,591,251 | 1/1997 | Brugger ............................ 604/122 X |

Primary Examiner—Gerald A. Michalsky
Attorney, Agent, or Firm—Thomas Schneck; Kenneth C. Brooks

[57] ABSTRACT

Provided is a gravity feed flow controller in which fluid communication with a particle sensor allows gas bubbles, present in a liquid flowing therethrough, to escape, under influence of a buoyant force associated therewith, before entering the sensor.

20 Claims, 4 Drawing Sheets

FLOW CONTROLLER FOR A PARTICLE SENSOR

TECHNICAL FIELD

The present invention pertains to the field of particle sensors. Specifically, the present invention pertains to a flow controller used with a device for detecting particulates in water.

BACKGROUND ART

Particle detectors have been used for a variety of purposes to detect the presence and/or size of particles in various gases, including air. They have proved particularly useful to control contamination during precision manufacturing operations and are finding increasing use for determining the purity level of various liquids such as water. Determining the purity of liquids has become increasingly important in the semiconductor industry, because many of the fabrication processes use liquids. Any particulates contained in the liquids could contaminate the semiconductor products, thus reducing manufacturing yields.

Moreover, the present generation of microcomputers necessitates fabrication of electronics with components of ever decreasing sizes, making such components extremely susceptible to contamination of decreasing size. This has pushed the semiconductor industry to promulgate much higher quality filtration standards for particle detectors to sense particulate matter. Instrumental to achieving these higher standards is increasing the accuracy of the particle detectors by preventing the detection of bodies in the liquid which have a negligible effect on semiconductor manufacturing processes. One such body is gas present in the liquid.

Detecting gas bubbles in liquid can provide a false indication of the presence of particulate matter in the liquid. This can greatly increase the cost of manufacture of semiconductor products. A liquid might incorrectly be determined to be unsuitable for a manufacturing step, resulting in premature disposal and/or replacement. Therefore, it would be advantageous to remove bubbles from liquids which are being examined for the presence of particulate matter. Many prior art attempts have been made to separate bubbles from liquids.

U.S. Pat. No. 5,422,003 discloses a gas/liquid separation flow regulator which carries out gas/liquid separation by preventing an uncontrolled flow of sewage and facilitates control of liquid flow. The outer shell of the gas/liquid separation flow rate regulator is cylindrical in shape with its inner periphery providing a cylindrical surface. An edge inclining unidirectionally from one end to the other is formed at the upper edge of a partition plate for dividing the cylindrical shell into two chambers. The lower end of this inclined edge is butted to the cylindrical surface of the cylindrical member so as to form an overflow weir. A return port is centrally located on the cylindrical member and is disposed on the opposite side of the surface of the cylindrical member facing the overflow weir.

U.S. Pat. No. 5,338,341 discloses a separator for removing gases from water. An elongated tube having a cylindrical wall houses a concentric separator tube of a smaller diameter, leaving a vortex region between them. Water containing gas is tangentially injected into the vortex region, flowing downwardly to an exit port. In this manner, a vortex is formed within the separator which allows gases to collect at the top and be released by a valve.

U.S. Pat. No. 5,332,100 discloses a flotation method for separating mineral ores in a slurry. The slurry is introduced under pressure into the top of a first column through a downwardly facing nozzle, and gas is entrained into the slurry forming a downwardly moving foam bed in the first column. The foam bed passes from the bottom of the first column into a second column concentrically disposed about the first column. The gas and liquid separate in the second column, with the gas carrying particles upwardly, over a weir. The liquid/gas interface level in the second column is kept above the bottom of the first column, and an air flow rate into the top of the first column is controlled to keep the first column substantially full of foam.

U.S. Pat. No. 5,123,938 discloses a device for separating air from water and discharging the separated air. The device includes a housing with a feed aperture and a discharge aperture for the liquid to be degassed. The internal space of the housing is at least partially filled with open filling elements which have a large surface area relative to the used volume. The air present in water adheres to the surface of the filling element and forms little bubbles. The small bubbles increase into larger bubbles by coalescence, until they have sufficient floating power to break away from the filling element and rise to the surface of the water. The air is subsequently released through a valve in the top of the device.

U.S. Pat. Nos. 4,585,465 and 4,643,746 each discloses a method and device for causing bubbles in a fluid to coalesce into a coherent mass. The device discloses a cylindrical chamber having an input to allow fluid to tangentially enter the chamber. Fluid entering the chamber creates a vortex which flows from one end of the chamber to the other.

U.S. Pat. No. 4,102,655 discloses a bubble trap for removing bubbles from liquids, such as blood. The bubble trap includes a closed container for holding liquid, an inlet extending through the container bottom upwardly within the container to an inlet opening space below the container top. The container has a larger cross-sectional area than the inlet itself. An outlet extends through the container top downwardly within the container to an outlet opening, with the outlet opening being lower in the container than the inlet opening. Liquid flowing upwardly through the inlet opening into the container subsequently flows downwardly to reach the outlet opening. In this fashion, gas bubbles present in the liquid entering the inlet are allowed to rise above the surface of the liquid in the container, before passing through the outlet opening.

A drawback with the aforementioned devices is that the initial particle distribution in the liquid is disrupted to remove bubbles therefrom.

It is an object of the present invention, therefore, to provide an improved particle sensor having a device for removing bubbles from the stream of liquid entering the particle sensor while maintaining the original particle distribution in the liquid flow.

It is another object of the present invention to maintain a constant flow rate through a particle sensor while removing bubbles from liquid entering therein.

SUMMARY OF THE INVENTION

These objects have been achieved by providing a gravity feed flow controller in fluid communication with a particle sensor which allows gas bubbles, present in a liquid flowing therethrough, to escape, under influence of a buoyant force associated therewith, before entering the sensor. The flow controller includes a hollow body and a flow regulator in fluid communication with the hollow body via the particle sensor. The hollow body includes a longitudinal axis extending parallel to a force of gravity with liquid flowing from a supply into an inlet forming a stream that travels under a force of gravity through an outlet, into the sensor. Liquid exiting the sensor flows through an orifice in the flow regulator, emptying into a drain. The inlet must be positioned sufficiently distant from the outlet to allow a buoyancy force associated with bubbles of a predetermined diameter to float against gravity, and therefore, the liquid flow to escape therefrom. Disposed above the inlet is a vent portion which typically includes an opening connecting to an ambient atmosphere. Bubbles escaping from the liquid travel through the opening. Disposed between the vent portion and the inlet is an overflow aperture, with the hollow body extending therebetween defining a volume. Liquid enters the inlet at a first rate and exits the flow regulator at a second rate, with the rate of flow of the liquid stream passing between the inlet and the outlet being proportional to the difference between the first rate and the second rate, as well as the force of gravity acting upon the liquid present in the volume. In this manner, a constant flow rate is achieved through the particle sensor.

In another embodiment, the hollow body may have an adjustable length to control the flow rate of the stream between the inlet and outlet. Alternatively, the flow regulator may be slidably engaged with the hollow body to adjust the flow rate of the stream, with the adjustment of the flow rate being dependent upon the change in distance between the overflow aperture and the orifice of the flow regulator.

BEST MODE FOR CARRYING OUT THE INVENTION

Figure 1:
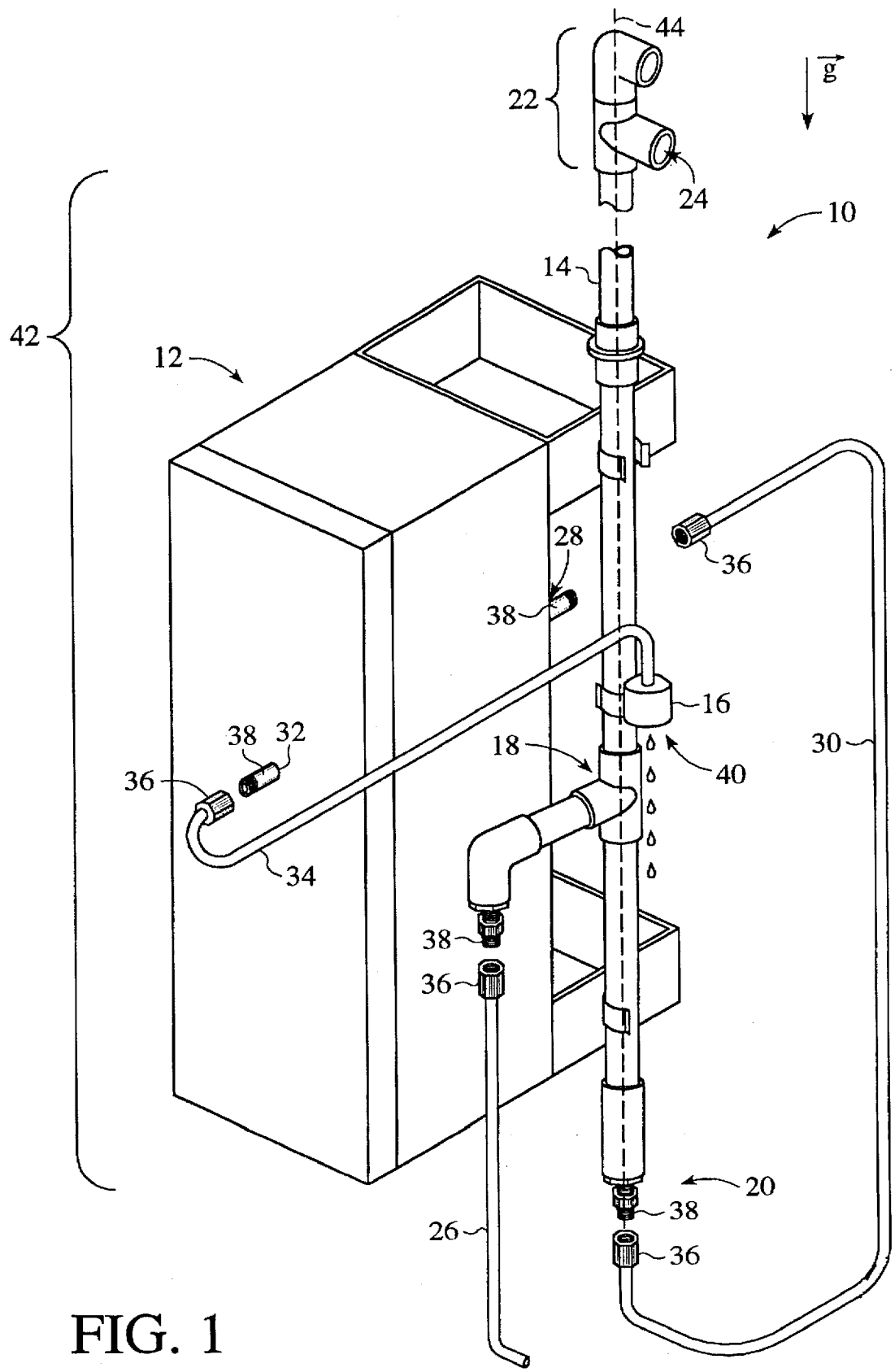
FIG. 1 is a perspective view of the present invention in accord with a preferred embodiment.

With reference to FIG. 1, the present invention includes a gravity feed flow controller 10 in fluid communication with a particle sensor 12. Flow controller 10 includes a hollow body 14 and a flow regulator 16. Flow regulator 16 includes an orifice 40. Hollow body 14 includes an inlet 18, an outlet 20, a vent portion 22 and an overflow aperture 24. Outlet 20 is in constant fluid communication with a fluid input 28 of sensor 12 via conduit 30. An additional sensor (not shown) may be connected to flow controller 10 vis-a-vis a second outlet 23 positioned proximate to outlet 20, shown more clearly in FIG. 2. Inlet 18 is in constant fluid communication with a supply of liquid, shown more clearly in FIG. 4, via conduit 26.

Returning again to FIG. 1, a fluid output 32 of sensor 12 is in constant fluid communication with flow regulator 16 via conduit 34. Conduits 26, 30 and 34 connect between the various elements of the flow controller 10, sensor 12 and supply of liquid in any reasonable manner capable of making a fluid-tight seal. Typically, compression nuts 36 are disposed at the opposed ends of conduits 26, 30 and 34 and are threaded onto taps 38 associated with hollow body 14 and sensor 12. Conduits 26, 30 and 34 are typically formed from tubing having a ¼ inch diameter. Although hollow body 14 may take any shape as desired, it is preferable that hollow body 14 have a cylindrical shape with a ½ inch inside diameter.

Figure 2:
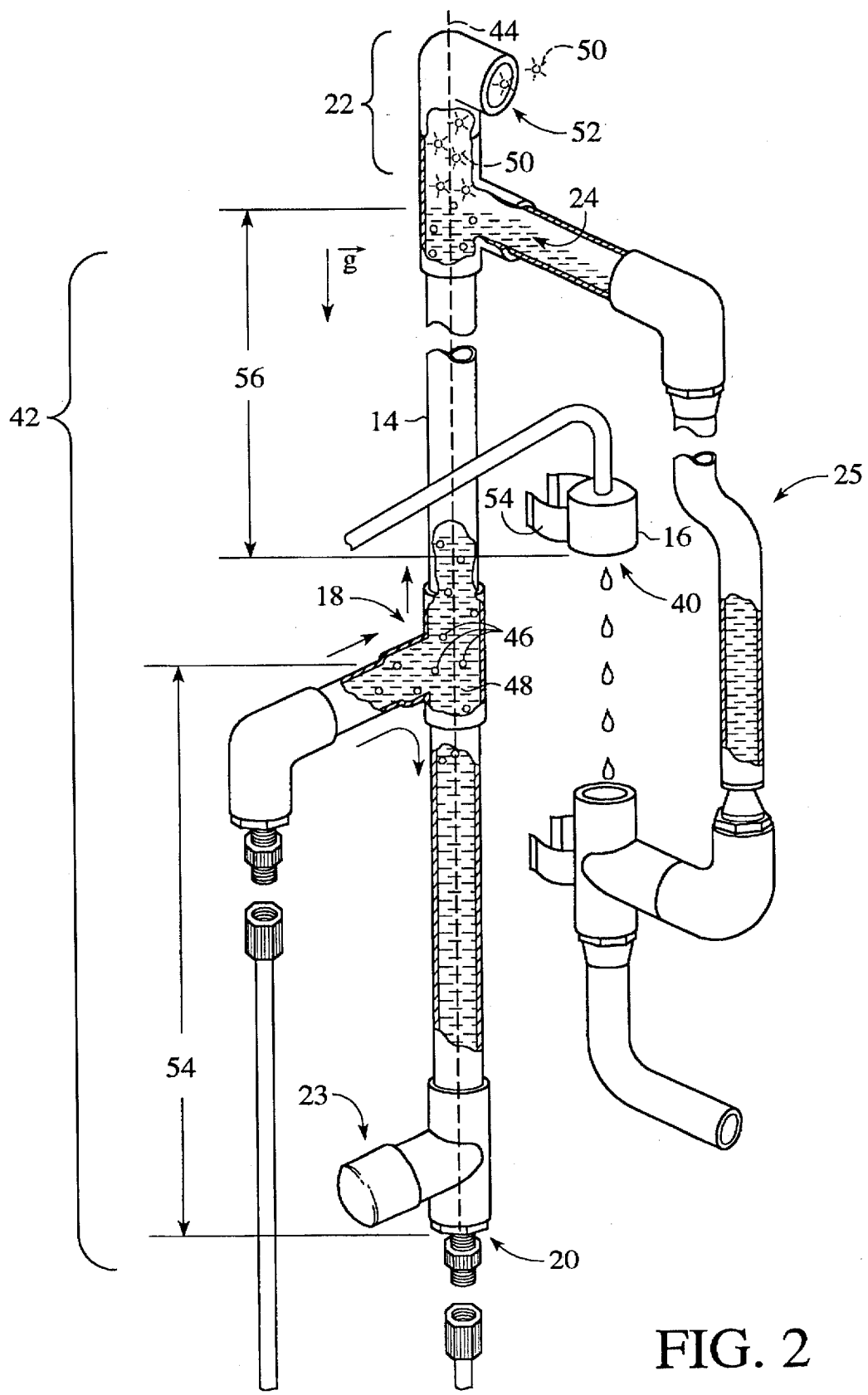
FIG. 2 is a partial cutaway perspective view of the invention shown in FIG. 1.

Referring also to FIG. 2, inlet 18 is adapted so that liquid flowing through conduit 26 enters hollow body 14 at a first predetermined flow rate. Orifice 40 is adapted so that liquid exits therefrom at a second predetermined flow rate, with the first predetermined flow rate being greater than the second predetermined flow rate. The difference between the first and second predetermined flow rates is chosen such that liquid entering inlet 18 fills a volume 42 of hollow body 14 which extends between outlet 20 and overflow aperture 24. It is preferred that the liquid in volume 42 exit through outlet 20 under influence of gravity. To that end, hollow body 14 includes a longitudinal axis 44 that is parallel to a force of gravity $\overline{g}$. Excess liquid entering volume 42 traverses overflow aperture 24, exiting hollow body 14. This design facilitates providing a constant pressure on liquid exiting outlet 20, because both the mass of the liquid and gravity are constant. The quantity of liquid 48 in volume 42 is kept constant by removing excess liquid 48 through overflow aperture 24. By maintaining a constant pressure on the fluid in volume 42, a constant flow rate through fluid input 28 and fluid output 32 may be achieved, substantially independent of the first predetermined flow rate through inlet 18. A drain pipe 25 may be placed in fluid communication with both overflow aperture 24 and orifice 40 to direct liquid exiting the particle detector to the appropriate drainage system.

A constant flow rate is particularly important when detecting particles in a liquid in that it allows accurately determining the ratio of particulates to volume of liquid by sampling a small portion of the liquid being analyzed. If the flow rate of the liquid were not kept constant, an accurate determination as to how many particulates per unit measure would be difficult to ascertain. In addition, a constant flow rate allows the original particle distribution of particles in the liquid to be maintained. Disturbing the particle distribution in the liquid may result in an inaccurate measure of the particles detected. This is particularly true with respect to larger particles, particles of 10 microns or larger. These larger particles tend to fall out of solution when the liquid flow is stagnant, such as in the presence of baffles or varying flow rates. This would result in sensor 12 detecting less particulates than were actually present in the liquid. Periodically, the particles that fall out of solution become re-suspended causing random bursts, or high counts of particles being detected.

To ensure a constant flow rate and prevent disturbing the particle distribution, it is preferred that the inner bore of hollow body 14 be smooth and with a minimum number of ridges or protrusions. Similarly the interface between compression nuts 36, taps 38 and the conduits should have the same degree of smoothness as the inner bore of the hollow body 14, as well as inlet 18.

To further increase the accuracy of the sensor 12, the flow controller 10 is adapted to prevent the detection of gas bubbles 46 that may be entrained in a stream of liquid 48 passing through volume 42. Detection of gas bubbles 46 in stream 48 by sensor 12 can provide a false indication of the presence of particulate matter. Removing gas bubbles 46 from stream 48 is achieved by positioning outlet 20 of hollow body 14 downstream, and sufficiently distant, from inlet 18 so that a buoyant force associated with each of gas bubbles 46 allows them to escape, shown as 50, from stream 48 by moving into vent portion 22. In this fashion, the buoyant force associated with bubbles of a predetermined size moves against gravity $\overline{g}$. The buoyant force associated with bubbles 46 allows them to move through stream 48 at a particular speed which is dependent upon the bubble diameter and the viscosity of stream 48. The speed at which bubbles move from stream 48, proximate to inlet 18, toward vent portion 22 must be greater than the rate of flow of stream 48 from inlet 18 to outlet 20. Assuming a constant flow rate and viscosity of stream 48, the smallest diameter bubble that may escape from stream 48 is a function of a distance 54 between inlet 18 and outlet 20.

In a typical embodiment, stream 48 comprises of deionized water with the first predetermined flow rate through inlet 18 in the range of 200–2000 milliliters per minute, with 200 milliliters being the preferred rate. The second predetermined flow rate through orifice 40 of flow regulator 16 is in the range of 75–100 milliliters per minute, with 100 milliliters being the preferred rate. Thus, 100 milliliters per minute is the preferred flow rate of stream 48. With a distance of 25 inches between inlet 18 and outlet 20, bubbles 46 having a diameter of 0.5 microns and larger may be separated from stream 48.

Bubbles having a diameter smaller than 0.5 microns may be successfully removed from stream 48 by reducing the flow rate of the same. To that end, flow regulator 16 may be slidably engaged with the hollow body 14 via a clamp 54. Reducing a distance 56 between flow regulator 16 and overflow aperture 52 reduces the pressure-head, in volume 42, thereby reducing the flow rate of stream 48. Alternatively, by increasing a distance 56 between overflow aperture 24 and orifice 40, the flow rate of stream 48 would be increased, if desired. The increase in flow rate results from the increased pressure-head of the liquid in volume 42.

Figure 3:
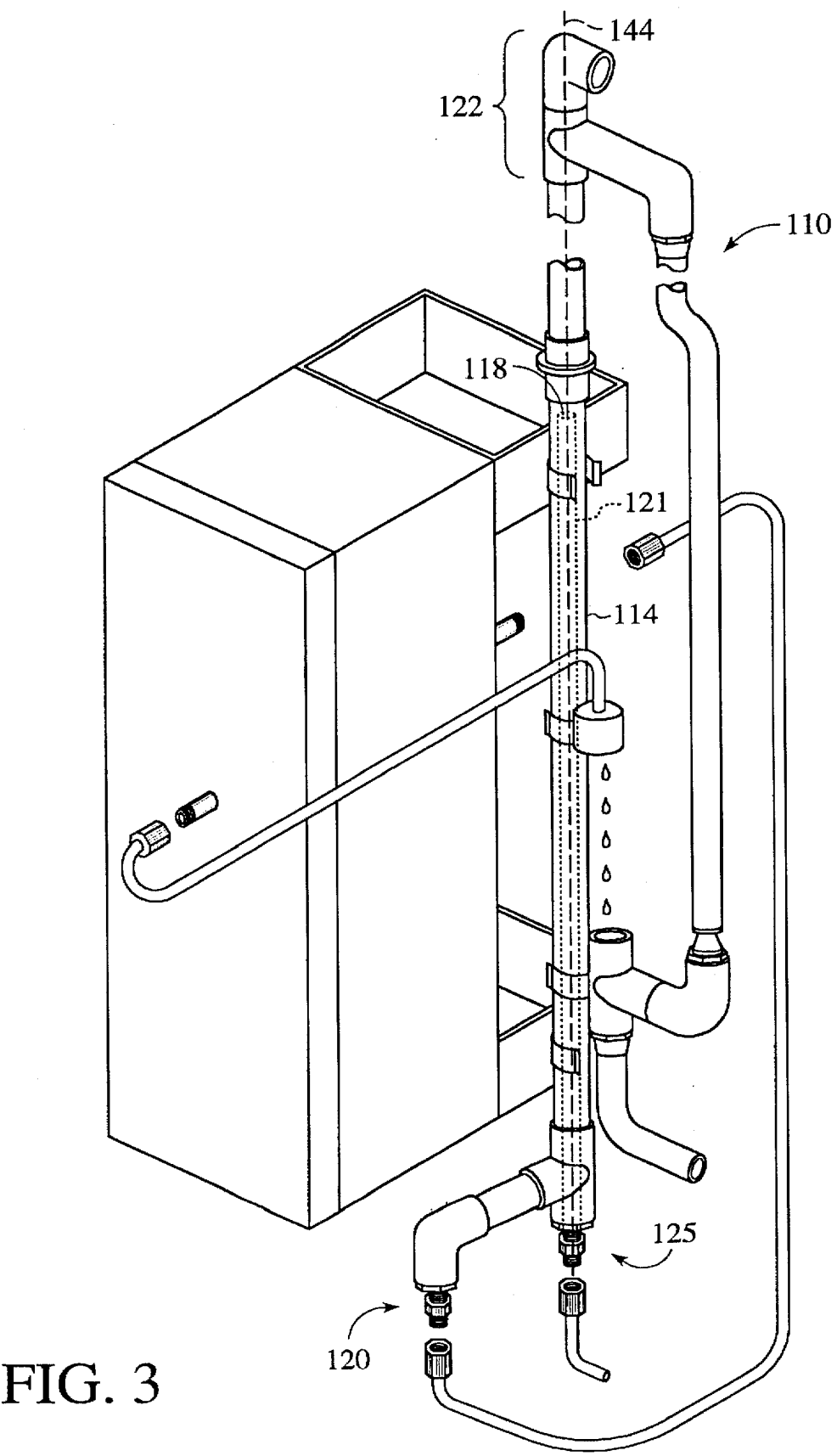
FIG. 3 is a side view showing an alternative embodiment of the present invention.

Referring also to FIG. 3, an alternate embodiment is shown in which a hollow riser tube 121 is disposed within hollow body 114. Typically, riser 121 is symmetrically disposed about axis 144. Riser 121 may be integrally formed with said hollow body and extends from aperture 125, positioned at one end of hollow body 114, toward vent portion 122, terminating in inlet 118. In this manner, fluid may enter hollow body 114 at a point proximate to outlet 120, while removing bubbles from fluid flow. This requires, as with inlet 18, placing inlet 118 sufficiently distant from outlet 120 so that a buoyant force associated with bubbles, escape from the stream, in body 114, by moving to vent portion 122. In operation, fluid flows through riser 121 and enters hollow body 114 by passing through inlet 118. Liquid passing through inlet 118 flows back toward outlet 120, with the bubbles in a stream moving as described above with respect to FIGS. 1 and 2. The advantage with this design is that the controller 110 can be made more compact by abrogating some of the additional fittings and protrusions which extend from hollow body 114.

Figure 4:
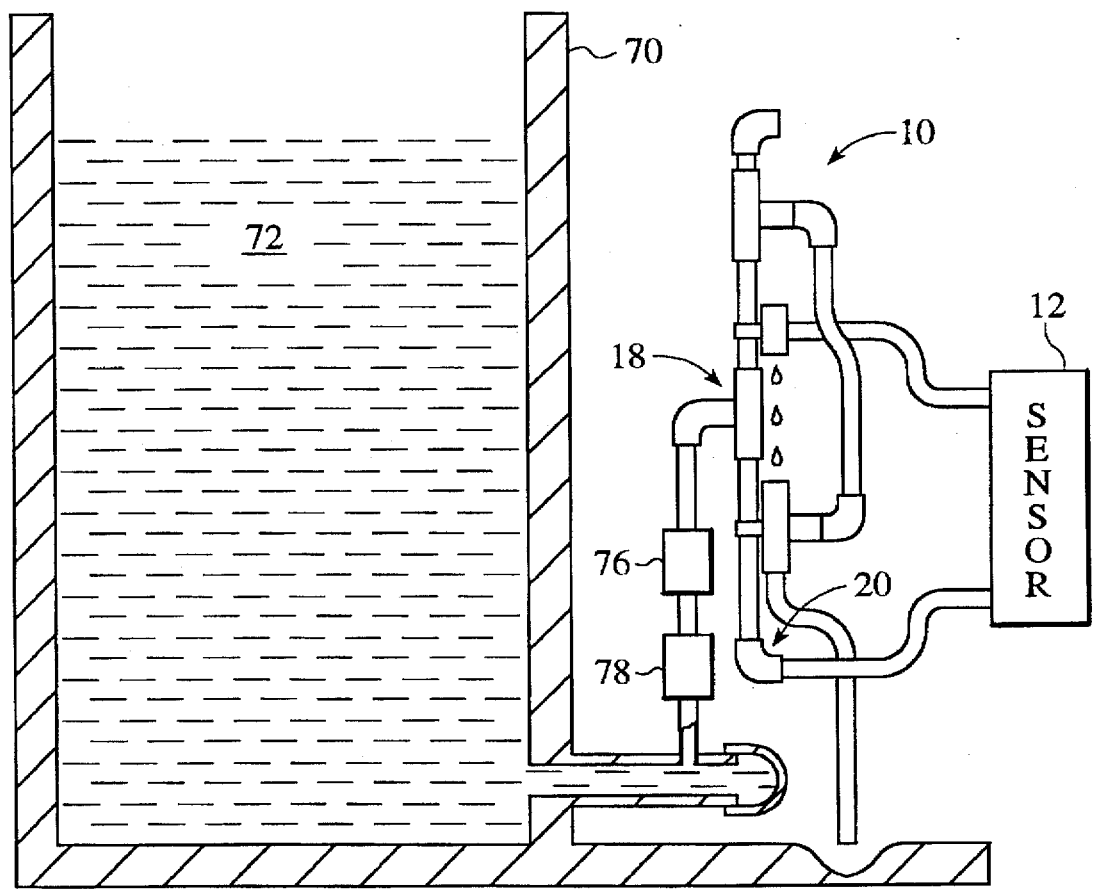
FIG. 4 is a side view of the proper attachment of the invention shown in FIGS. 1 and 2 with a supply of liquid.

Referring also to FIG. 4, typically, flow controller 10 will be mounted vertically on the outer surface of a tank 70 holding a supply of liquid 72. Sensor 12 may be mounted in any convenient position and is typically in electrical communication with a suitable power source. With the flow controller mounted vertically, liquid 72 is fed through both flow controller 10 and sensor 12 by gravity to achieve a constant flow rate therethrough. However, if desired, a pump 76 may be disposed between inlet 18 and tank 70 to create the stream flowing through flow controller 10. In addition, one or more particle filters 78 may be disposed between tank 70 and pump 76. With inlet 18 positioned with respect to outlet 20, as described above, a highly accurate particle detector is realized that is capable of separating particles from gas bubbles present in liquid 72.

I claim:

1. A flow controller for a particle sensor adapted to detect particulates in a supply of liquid having gas bubbles associated therewith, said particle sensor having a fluid input and a fluid output, with said flow controller comprising:

a hollow body having an outlet, a vent portion and an inlet, with said outlet disposed between said vent portion and said sensor and in fluid communication with said fluid input thereof, said inlet being in fluid communication with said supply of liquid; and a flow regulator in fluid communication with said fluid output of said sensor, thereby placing said hollow body in fluid communication with said flow regulator, said flow regulator having an orifice adapted to allow liquid to flow therethrough to form a stream of said liquid moving from said inlet to said outlet, with said inlet positioned upstream from said outlet, sufficiently distant therefrom, to allow a buoyant force associated with each of said gas bubbles, having a diameter within a specified range, to move away from said outlet, escaping from said stream by exiting through said vent portion.

2. The flow controller as recited in claim 1 wherein said inlet is adapted to allow liquid to enter therethrough at a first flow rate, and said orifice is adapted to allow liquid to exit therethrough at a second flow rate, with said first flow rate being greater than said second flow rate forming a fluid pressure within said hollow body.

3. The flow controller as recited in claim 2 wherein said first flow rate is in the range of 200 to 2000 milliliters per minute and said second flow rate is in the range of 50 to 100 milliliters per minute.

4. The flow controller as recited in claim 1 wherein said inlet is adapted to allow liquid to enter therethrough at a first flow rate, and said orifice is adapted to allow liquid to exit therethrough at a second flow rate, with said first flow rate being greater than said second flow rate forming a fluid pressure within said hollow body with a flow rate of said stream being proportional to said fluid pressure.

5. The flow controller as recited in claim 1 wherein said vent portion includes an opening in constant fluid communication with an ambient atmosphere, with said opening disposed above said inlet to prevent a portion of said stream from exiting therefrom.

6. The flow controller as recited in claim 1 wherein said specified range is 0.5 microns and greater.

7. The flow controller as recited in claim 1 wherein said flow regulator is in fluid communication with said supply of liquid, with liquid exiting said orifice thereby returning to said supply of liquid.

8. The flow controller as recited in claim 1 wherein said stream moves at a constant rate.

9. The flow controller as recited in claim 1 wherein said liquid is water.

10. The flow controller as recited in claim 1 wherein said hollow body has a circular cross-section.

11. A flow controller for a particle sensor adapted to detect particulates in a supply of liquid having gas bubbles associated therewith, said particle sensor having a fluid input and a fluid output, with said flow controller comprising:

a hollow body having a longitudinal axis extending parallel to a force of gravity, said body having an inlet, an outlet, a vent portion and an overflow aperture disposed between said vent portion and said inlet, with said inlet disposed between said overflow aperture and said outlet, said outlet in fluid communication with said fluid input of said sensor, and said inlet in fluid communication with said supply of liquid; and a flow regulator in fluid communication with said fluid output of said sensor, thereby placing said hollow body in fluid communication with said flow regulator, said flow regulator having an orifice adapted to allow liquid to flow therethrough, whereby said liquid flows between said inlet and said outlet under influence of said force of gravity, forming a stream having a flow rate, with said inlet positioned upstream from said outlet, sufficiently distant therefrom, to allow a buoyant force associated with each of said gas bubbles, having a diameter within a specified range, to move away from said outlet, escaping from said stream by exiting through said vent portion.

12. The flow controller as recited in claim 11 wherein said flow rate is constant and said flow regulator is slidably attached to said hollow body, with said constant flow rate being proportional to a distance between said orifice and said overflow aperture.

13. The flow controller as recited in claim 11 said liquid is deionized water.

14. The flow controller as recited in claim 11 wherein said hollow body has a circular cross-section.

15. The flow controller as recited in claim 11 wherein said flow regulator is in fluid communication with said supply of liquid, with liquid exiting said orifice returning to said supply of liquid.

16. The flow controller as recited in claim further including pump means, positioned between said supply of liquid and said inlet, for providing said flow rate.

17. A flow controller for a particle sensor adapted to detect particulates in a supply of liquid having gas bubbles associated therewith, said particle sensor having a fluid input and a fluid output, with said flow controller comprising:

a hollow body having an outlet, a vent portion and an aperture;

a riser tube, disposed within said hollow body, said riser tube extending from said aperture toward said vent portion, terminating in an opening, said opening being disposed between said vent portion and said outlet, with said outlet being in fluid communication with said fluid input of said sensor and said aperture being in fluid communication with said supply of liquid and adapted to allow liquid to enter therethrough, and pass through said riser tube to exit said opening; and a flow regulator in fluid communication with said fluid output of said sensor, thereby placing said hollow body in fluid communication with said flow regulator, said flow regulator having an orifice to allow liquid to flow therethrough, whereby a stream having a constant flow rate moves through said hollow body and said riser tube.

18. The flow controller as recited in claim 17 wherein said opening is positioned upstream from said outlet, sufficiently distant therefrom, to allow a buoyant force associated with each of said gas bubbles, having a diameter within a specified range, to move away from said outlet, escaping from said stream by exiting through said vent portion.

19. The flow controller as recited in claim 17 wherein said opening is adapted to allow liquid to enter therethrough at a first rate and said outlet is adapted to allow liquid to exit therethrough at a second rate, with said first rate being greater than said second rate forming a fluid pressure within said hollow body, with said pressure being proportional to a difference between said first rate and said second rate, said pressure defining a flow rate.

20. The flow controller as recited in claim 19 wherein said first rate is in the range of 200 to 2000 milliliters per minute, said second rate is in the range of 50 to 100 milliliters per minute and said specified range is 0.5 microns and greater.

* * * * *

UNITED STATES PATENT AND TRADEMARK OFFICE
CERTIFICATE OF CORRECTION

PATENT NO. : 5,664,599
DATED : Sep. 9, 1997
INVENTOR(S) : D. John Hunt

It is certified that error appears in the above-identified patent and that said Letters Patent is hereby corrected as shown below:

Col. 4, line 13, " $\overline{g}$ " should read -- $\vec{g}$ --.

Col. 4, line 64, " $\overline{g}$ " should read -- $\vec{g}$ --.

Claim 16, col. 7, line 23, "as recited in claim further" should read -- as recited in claim 15 further --.

Signed and Sealed this

Third Day of March, 1998

Attest:

BRUCE LEHMAN

*Attesting Officer*      Commissioner of Patents and Trademarks